United States Patent
Thomas et al.

(12)

(10) Patent No.: US 6,395,476 B1
(45) Date of Patent: May 28, 2002

(54) METHODS OF PREDICTING THE OUTCOME OF HBV INFECTION

(75) Inventors: Howard C. Thomas; John A. Summerfield; Janice Main, all of London (GB)

(73) Assignee: Imperial College of Science Technology & Medicine, London (GB)

( * ) Notice: Subject to any disclaimer, the term of this patent is extended or adjusted under 35 U.S.C. 154(b) by 0 days.

(21) Appl. No.: 09/031,952

(22) Filed: Jan. 27, 1998

Related U.S. Application Data

(63) Continuation of application No. PCT/GB96/01819, filed on Jul. 25, 1996.

(30) Foreign Application Priority Data

Jul. 27, 1995 (GB) .............................................. 9515393
Oct. 13, 1995 (GB) .............................................. 9521025
Jul. 9, 1996 (GB) .............................................. 9614414

(51) Int. Cl.[7] .......................... C12Q 1/68; C07H 21/02; C07H 21/04
(52) U.S. Cl. .......................... 435/6; 536/23.1; 536/23.5; 536/24.33
(58) Field of Search ................. 435/6, 69.1; 530/390.1; 514/885, 44; 526/23.1; 536/23.1, 24.33, 23.5

(56) References Cited

U.S. PATENT DOCUMENTS 5,270,199 A * 12/1993 Ezekowitz et al. ...... 435/240.2

FOREIGN PATENT DOCUMENTS

| WO | 89/01519 | 2/1989 |
| WO | 92/07579 | 5/1992 |

OTHER PUBLICATIONS

Guelfi JD. Encephale. 21 Spec (5): abstract, Dec. 1995.*
Miller et al. FASEB. 9: 190–99, Feb. 1995.*
Mulligan RC. Science. 260: 926931, May 1993.*
Merwin et al. Bioconjug Chem. 5(6): abstract Nov. 1994.*
Orkin et al. Report and Recommendations of the Panel to Assess the NIH Investment in Research on Gene Therapy, Dec. 1995.*
Eck et al. Chapter 5, Goodman's and Gilman's The Pharmacological Basis of Therapeutics. 9th Ed. pp. 77–101, 1995.*
Thompson C. Science. 269: 301–302, Jul. 1995.*
Ezekowitz et al. Accession A59564, 109220, 109221, Q53530, 1989.*
GibcoBRL Life Technologies Catalogue and Reference Guide. pp. 11–18, 1993.*
Roemer et al. Eur. J. Biochem. 208: 211–215, 1992.*
Madsen et al, "A new frequent allele is the missing link in . . . ," Immunogenetics, vol. 40, pp. 37–44 (1994).
Sumiya et al, "Molecular Basis of opsonic defect . . . ," Lancet, vol. 337, pp. 1569–1570 (1992).
Lipscombe et al, "High frequencies in African and . . . ," Human Mol. Genetics, vol. 1, No. 9, pp. 709–715 (1992).
Madsen et al, "Interplay Between Promoter and Structural . . . ," J. Immunology, pp. 3013–3029 (1995).
Summerfield et al, "Mannose binding protein gene mutations . . . ," vol. 345, pp. 886–889 (1995). Lancet.
Tobi et al, "Prolonged Atypical Illness Associated . . . ," Lancet, pp. 61–64 (1982).
Kuhlman et al, "The Human Mannose–Binding . . . ," J. Exp. Med., vol. 169, pp. 1733–1745 (1989).
Ohta et al, "The Mechanism of Carbohydrate . . . ," J. Biol. Chem., vol. 265, pp. 1980–1984 (1990).
Matsushita et al, "Activation of the Classical Complement . . . ," J. Exp. Med., vol. 176, pp. 1497–1502 (1992).
Super et al, "The level of mannan–binding protein . . . ," Clin. Exp. Immunol., vol. 79, pp. 144–150 (1990).
Hartshorn et al, "Human Mannose–binding Protein . . . ," J. Clin. Invest., vol. 91, pp. 1414–1420 (1993).
Thursz et al, "Association Between an MHC Class . . . ," New Eng. J. Med., vol. 332, pp. 1065–1069 (1995).
Fukuda et al, :"The Chronic Fatigue Syndrome . . . ," Ann. Inter. Med., vol. 121, pp. 953–959 (1994).
David et al, "Postviral fatigue syndrome . . . ," Br. Med. J., vol. 296, pp. 696–698 (1988).
Ramsey et al, "Encephalomyelitis Simulating Poliomyelitis," Lancet, pp. 761–764 (1956).
McEvedy et al, "Royal Free Epidemic of 1955: A Reconsideration," Br. Med. J., vol. 1, pp. 7–11 (1970).
Yousef et al, "Chronic Enterovirus Infection in Patients with Postviral . . . ," Lancet, pp. 146–150 (1988).
Archard et al, "Postviral fatigue syndrome . . . ," J. Roy. Soc. Med., vol. 81, pp. 326–329 (1988).
Behan et al, "The postviral fatigue syndrome—an analysis . . . ," J. Infect., vol. 10, pp. 211–222 (1985).
Manu et al, "The Pathophysiology of Chronic Fatigue . . . ," Int. J. Psychiatry Med., vol. 22, pp. 397–408 (1982).
Abrauaya et al, "Detection of point mutations with a modified . . . ," Nucleic Acid. Res., vol. 23, pp. 675–682 (1995).
Dore et al, "Increased insulin–like growth factor . . . ," Arthritis & Rheumatism, vol. 38, pp. 110–114 (1995).
Wordsworth et al, "HLA–DR typing using DAN amplification . . . ," Immunogenetics, vol. 32, pp. 413–418 (1990).
Kilpatrick et al, "Association between mannan binding . . . ," Human Reproduction, vol. 10, pp. 2501–2505 (1995).

(List continued on next page.)

Primary Examiner—Deborah Crouch
Assistant Examiner— Joseph Woitach
(74) Attorney, Agent, or Firm—Nixon & Vanderhye

(57) ABSTRACT

Methods for predicting the outcome of infection of HBV are provided, as well as kits for use in such methods. In particular, methods which comprise determination of the presence of mutations in exon 1 of the gene coding for the human MBP gene are provided.

24 Claims, 1 Drawing Sheet

OTHER PUBLICATIONS

Figure 1:
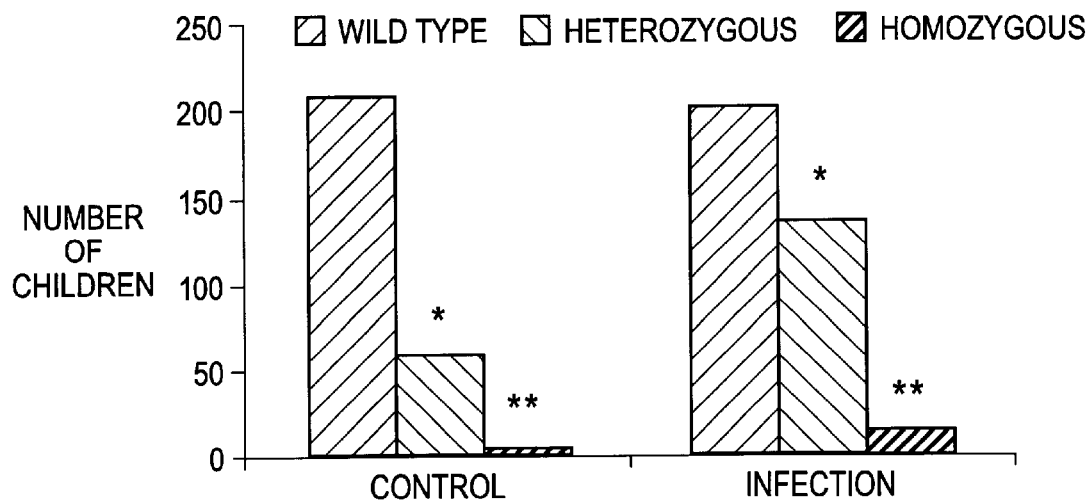

Lipscombe et al, "Mutations in the Human Mannose . . . ," Eur. J. Hum. Genetics, vol. 4, pp. 13–19 (1996).

Clements et al, "Detection of Enterovirus–Specific RNA in Serum: . . . ," J. Med. Virol., pp. 156–0161 (1995).

Galbraith et al, "Phylogenetic analysis of short enteroviral . . . ," J. Gen. Virol., vol. 76, pp. 1701–1707 (1995).

Straus et al, "Acyclovir Treatment of the Chronic . . . ," N. Eng. J. Med., vol. 319, pp. 1692–1698 (1988).

Peterson et al, "A Controlled Trial of Intravenous . . . ," Am. J. Med., vol. 89, pp. 554–560 (1990).

Lloyd et al, "A Double–Blind, Placebo–Controlled Trial . . . ," Am. J. Med., vol. 89, pp. 561–568 (1990).

Brook et al, "Interferon–60 Therapy for Patients with Chronic . . . ," J. Infect. Dis., vol. 168, pp. 791–792 (1993).

* cited by examiner

METHODS OF PREDICTING THE OUTCOME OF HBV INFECTION

This is a continuation of PCT application No. PCT/GB96/01819, filed Jul. 25, 1996.

The present invention relates to methods of predicting the outcome of infection. In particular it relates to methods for predicting the outcome of viral infections, including HBV infection, as well as methods for determining the susceptibility of children to infection. The invention also includes kits for use in such methods.

Mannose binding protein (MBP) is a calcium dependent lectin that plays an important role in innate immunity both by activating complement and phagocytosis, using an MBP associated serine protease (MASP), and acting directly as an opsonin by binding to collectin receptors through the collagen domain of MB?(Taylor et al, Biochem. J. 262:763–771 (1989); Kuhlman et al, J. Exp. Med., 169:1733–1745 (1989); Ohta et al, J. Biol. Chem., 265:1980–1984 (1990); Matsushita, M. and Fujita, T., J. Exp. Med., 176:1497–1502 (1992); Super et al, Clin. Exp. Immunol., 79:144–150 (1990); Malhotra et al, Biochem. J., 293:15–19 (1993)). MBP binds to carbohydrate moieties on various pathogens including influenza A virus (Hartshorn et al, J. Clin. Invest., 91:1414–1420 (1993)). Point mutations in codons 54 and 57 of the MBP gene are associated with low serum levels of MBP and a common immunodeficiency caused by an opsonic defect (Sumiya et al, Lancet, 337:1569–1570 (1992); Lipscombe et al, Human Mol. Genet., 1:709–715 (1992)). A less common mutation in codon 52 has also been reported in associated with low serum MBP levels (Madsen et al, Immunogenetics, 40:37–44 (1994)). Serum MBP levels may also be modulated by promoter polymorphisms (Madsen et al, J. Immunology, 3013–3020 (1995)). The mutations have been associated with severe and unusual infections in children and adults (Sumiya et al, (1992), supra; Summerfield et al, Lancet, 345:886–889 (1995); Garred et al, Lancet, 346:941–943 (1995)).

WO-A-8901519 discloses the sequence of human mannose binding protein, and its cloning. WO-A-9207579 discloses recombinantly produced portions of mannose binding proteins, including human mannose binding protein.

We have now shown a clear linkage between mutations in the gene coding for MBP and a subject's susceptibility to infection.

Thus, in a first aspect the present invention provides a method of predicting and/or assessing the susceptibility of a subject to infection which comprises the step of determining whether the subject carries one or more mutations of the MBP gene.

Chronic fatigue syndrome is a condition of unknown aetiology, characterised by physical and mental fatigue, with other symptoms including myalgia. The symptoms typically follow a viral infection, which is often glandular fever or influenza-like. It has been suggested that persistent virus infections with EBV (Tobi, et al, Lancet, :61–4 (1982)), HHV6 or enteroviral infection (Behan, et al, J. Infect, 10:211–222 (1985)) could account for the syndrome, but others have suggested that the subjective nature of the symptoms, and occurrence of other symptoms such as altered sleeping pattern, are more typical of depressive disease or somatisation disorder (Manu, et al, Int. J. Psychiatry Med., 22:397–408 (1992)).

We have now shown that development of chronic fatigue syndrome is linked with the same mutation in the MBP gene. This predisposition seems to be linked to a susceptibility to chronic viral infection generally.

Thus, in a second aspect, the present invention provides a method of predicting and/or assessing the susceptibility of a subject to develop a chronic viral infection which comprises the step of determining whether the subject carries the codon 52 mutation of the MBP gene.

In a third aspect, the present invention provides a method of predicting and/or assessing the susceptibility of a subject to develop chronic fatigue syndrome which comprises the step of determining whether the subject carries the codon 52 mutation of the MBP gene.

In a fourth aspect, the present invention provides a method of diagnosing chronic fatigue syndrome in a subject which comprises the step of determining whether the subject carries the codon 52 mutation of the MBP gene.

Thus, there are provided, for the first time, clear methods for assessing patients with respect to their susceptibity to viral infections and subsequent development of chronic fatigue syndrome, as well as methods for diagnosing chronic fatigue syndrome in patients presenting with the symptoms thereof.

In addition, it will be possible to assess patients who have already contracted a viral infection, and this may lead to the ability to preempt development of the syndrome by treatment with non-mutant mannose binding protein.

In addition, there are clear similarities and overlap in the symptom complex of chronic fatigue syndrome and other conditions such as depressive disease, irritable bowel syndrome ad Gulf war syndrome. Therefore, it is believed that identification of the codon 52 mutation will also indicate a susceptibility to develop such conditions.

Thus, in a fifth aspect, the present invention provides a method of predicting and/or assessing the susceptibility of a subject to develop depressive disease, irritable bowel syndrome and/or gulf war syndrome, which comprises the step of determining whether the subject carries the codon 52 mutation of the MBP gene.

Exposure to hepatitis B virus (HBV) causes either no infection, fulminant hepatitis, a self limiting acute hepatitis or a chronic persistent infection that may progress to cirrhosis and/or hepatocellular carcinoma. The reasons for this variation in natural history of HBV are unknown but are probably determined by host immune factors.

The middle surface protein of the HBV envelope contains a mannose rich oligosaccharide that would bind to MBP (Gerlich, W. Structure and Molecular Biology; In viral Hepatitis, ed. Zuckerman A. J., Thomas H. C.; Churchill Livingstone page 93 (1993)) and previous studies in patients with chronic HBV have shown a serum opsonic defect (Munoz L., PhD thesis, (1989) University of London, page 89).

Clearly, it would be advantageous for a physician to be able to predict the whether a particular subject is likely to develop a chronic HBV infection.

We have now shown that development of chronic HBV infection is linked with mutations in MBP.

Thus, in a sixth aspect, the present invention provides a method of predicting the outcome of HBV infection in a subject which comprises the step of determining whether the subject carries a mutation in the MBP gene.

In a seventh aspect, the invention provides a method of predicting the susceptibility of a subject to development of chronic HBV infection which comprises the step of determining whether the subject carries a mutation in the MBP gene.

In an eighth aspect, the present invention provides a method of predicting the susceptibility of a subject to HBV infection and/or development of acute HBV infection which comprises the step of determining whether the subject carries a mutation in the MBP gene.

In particular, these methods of the invention will comprise a determination of the presence of a mutation at codon 52 of exon 1 of the MBP gene.

The ability to determine whether a patient is likely to progress from acute to chronic HBV infection is of great use to the physician. Such patients can be treated earlier, before chronic HBV infection develops. This, in turn, should lead to better rates of response. Patients with acute HBV infection can simply be screened, and those carrying the mutation can be targeted for treatment.

In addition, individuals can be identified who are susceptible to HBV infection and are therefore in particular need of vaccination. Those identified as carrying the mutation can thus be the subject of targeted vaccination programmes.

Repeated bacterial and fungal infections associated with MBP mutations have been reported in children and adults suspected of having a ummunodeficiency syndrome (Sumiya et al, (1991), supra; Summerfield et al, *Lancet,* 345:886–889; Garred et al, *Lancet,* 346:941–943 (1995)). Both MBP mutations and childhood infections are common but as yet no clear link between the presence of such mutations and a predisposition to childhood infectins has been demonstrated.

We have now shown that such a link exists, and that testing for the presence of mutations in the mannose binding protein enables identification of those children more at risk of infectious disease, and particularly those children who possess a predisposition to recurrent infection.

Thus, in a ninth aspect, the present invention provides a method of determining whether a child is more likely to be susceptible to infection which comprises the step of determining whether the child carries at least one mutation in the MBP gene.

In a tenth aspect, the invention provides a method of determining whether a child is more likely to be susceptible to recurrent infection which comprises the step of determining whether the child carries at least one mutation the MBP gene.

In an eleventh aspect, the present invention provides a method of determining whether a baby is more likely to be born prematurely which comprises the step of determining whether the baby carries at least one mutation in the MBP gene.

In a twelfth aspect, the present invention provides a method of determining whether a child is more likely to be susceptible to infection which comprises the step of determining whether the child is homozygous for an MBP mutation. In the context of this aspect of the invention, homozygous refers either to the genotype or phenotype of the child with respect to MBP mutation. In other words, a child will be regarded as homozygous for MBP mutation even if it possesses a different mutation in each copy of the MBP gene.

In particular, these methods of the invention will comprise a determination of the presence of a mutation at codons 52, 54 or 57 of exon 1 of the MBP gene.

Suitably, in the methods of the present invention, the subject's genomic DNA will be extracted from a suitable source, e.g. from a blood sample, and the exon 1 region of the MBP gene will be amplified prior to analysis. Amplification can be carried out using various methods known to the skilled man, and include PCR, a technique well known to the skilled man, Ligase Chain Reaction (Abravaya et al, *Nucleic Acid Res.* 23: 675–82 (1995)), amplification refractory mutation system PCR (Davies et al, *Arthritis & Rheumatism,* 38: 110–114 (1995)) and site directed mutagenesis PCR (Madsen et al, *Immunogenetics* 40: 37–44 (1994)).

Mutations in the protein can also be detected by a variety of other means including direct DNA sequencing, Southern blot hybridisation or by using peptide specific antibodies, i.e. directed against the mutated protein.

In a further aspect, the present invention provides a kit for use in any of the methods of the invention which comprises one or more pairs of suitable primers for use in PCR amplification of the exon 1 region of the MBP gene.

Optionally, the kits of the invention further comprise one or more reagents/materials for use in establishing the MBP genotype of a subject. Examples of suitable reagents for establishing the genotype include primers for use in SSO dot-blot hybridization.

In yet further aspects, the present invention provides:

(a) the use of MBP in the preparation of a medicament for the prevention or treatment of a chronic viral infection;

(b) the use of MBP in the preparation of a medicament for the prevention or treatment of chronic fatigue syndrome;

(c) a method for the prevention or treatment of chronic fatigue syndrome which comprises administering to a subject an effective amount of MBP;

(d) a method for the prevention of a chronic viral infection which comprises administering to a subject an effective amount of MBP;

(e) the use of MBP in the preparation of a medicament for the treatment of HBV infection;

(f) the use of MBP in the preparation of a medicament for the prevention of acute HBV infection;

(g) the use of MBP in the preparation of a medicament to prevent development of chronic HBV infection;

(h) a method for the treatment of HBV infection which comprises administering to a subject an effective amount of MBP;

(i) a method for the prevention of acute HBV infection which comprises administering to a subject an effective amount of MBP; and (j) a method for preventing development of chronic HBV infection which comprises administering to a subject an effective amount of MBP.

(k) a method for the treatment of recurrent infection in a child which comprises administering to the child an effective amount of MBP.

Given that a clear link has been established between the codon 52, 54 and 57 mutations of the MBP gene and the appearance of certain conditions, the possibility exists that patients could be treated by one or other forms of "gene therapy". In this way a patients defective MBP gene could be corrected/repaired/replaced resulting in the provision of normal MBP in the patient.

In an additional aspect the present invention therefore provides:

(I) the use of DNA encoding the normal form of the MBP gene in the manufacture of a medicament for use in the prevention or treatment of:
(i) a chronic viral infection, eg chronic HBV infection;
(ii) chronic fatigue syndrome;
(iii) depressive disease;
(iv) irritable bowel syndrome;
(v) gulf war syndrome; and/or
(vi) recurrent infection, particularly bacterial or fungal infection.

In the methods of the present invention a suitable pair of primers for performing PCR amplification of the DNA sample are:

5' primer: 5'-GCACCCAGATTGTAGGACAGAG-3' SEQ ID NO.:1; and

3' primer: 5'-CAGGCAGTTTCCTCTGGAAGG-3' SEQ ID NO.:2 and these primers form yet a further aspect of the present invention.

In another embodiment determination of a subject's genotype is conveniently carried out using sequence-specific oligonucleotide (SSO) dot-blot hybridization and suitable primers are as follows:

codon 52 wild type: 5'-GATGGGCGTGATG-3' SEQ ID NO.:3;

codon 52 mutant: 5'-GATGGGTGTGATG-3' SEQ ID NO.:4;

codon 54 wild type: 5'-GTGATGGCACCAA-3' SEQ ID NO.:5;

codon 54 mutant: 5'-GTGATGACACCAA-3' SEQ ID NO.:6;

codon 57 wild type: 5'-ACCAAGGGAGAAAAG-3' SEQ ID NO.:7; and codon 57 mutant: 5'-ACCAAGGAAGAAAAG-3' SEQ ID NO.:8 and these primers form another aspect of the present invention.

Preferred features of each aspect of the invention are as for each other aspect *mutatis mutandis*.

The invention will now be described with reference to the following examples, which should not be construed as in any way limited the invention.

Figure 2:
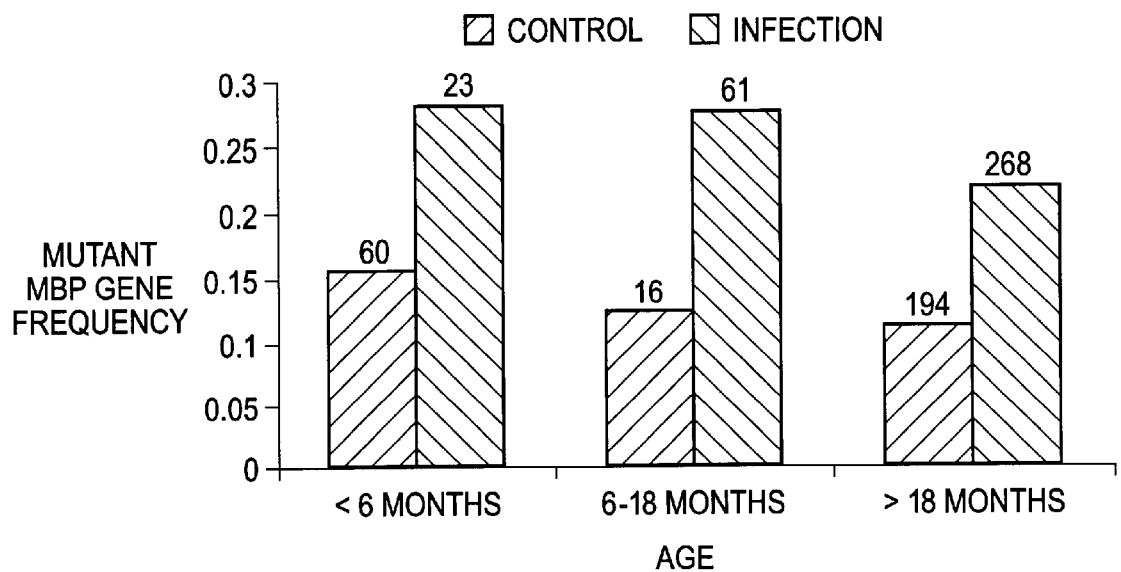

Example 1 refers to the figures in which:

FIG. 1: shows MBP genotypes in control children and children with infection; significantly more children with infection were heterozygous (*p=0.000004) or homozygous (**p=0.02) for MBP mutations; and FIG. 2: shows the frequency of MBP gene mutations in infected and control children from different age groups; the frequency of MBP mutations was significantly greater in the infected children below 6 months (p=0.05), between 6 and 18 months (p=0.03) and older than 18 months (p=0.0001), with the numbers indicating the size of the groups.

EXAMPLE 1

Methods

Blood samples were obtained from consecutive children attending paediatric outpatients or admitted to the general paediatric wards, the paediatric intensive care unit or neonatal intensive care unit of St Mary's Hospital. All were venesected for clinical reasons and up to four drops of surplus blood was spotted onto blotting paper (Guthrie cards) which was placed in an envelope and allowed to dry.

The information collected included the child's sex, date of birth, ethnic origin and provisional diagnosis. The diagnosis was confirmed by inspection of the notes or the clinical diagnostic codes in the hospital's computerised patient administration system, the study was approved by the Ethics Committee of Parkside Health Authority.

MBP genotypes were determined by analysis of DNA extracted from the dried blood spots. The Guthrie cards were autoclaved at 120° C. for 7 min and stored at room temperature. For DNA extraction, squares (~3 mm) were cut from the dried blood spots with a clean blade and boiled in 100 $\mu$l 1×PCR buffer for 7 min. Using 25–30 $\mu$l of the supernatant exon 1 of the MBP gene was amplified by PCR to yield a product of 338 bp (sumiya et al. (1991) supra). The genotype was determined by sequence specific oligonucleotide hybridization (Wordsworth et al, *Immunogenetics*, 32:413–418 (1990)).

Gene frequencies were determined and compared to expected frequencies using the Hardy Weinberg equation. Differences were evaluated using the Chi Square test, odds ratios and 95% confidence intervals. Children with the three different MBP mutations were grouped together for statistical analysis.

Results

Six hundred and ninety blood samples were collected. Forty five were duplicates, in 2 clinical details were inadequate and in 17 (2.5%) MBP genotyping failed. These samples were purged from the database before analysis. Data from the remaining 626 children (91%) were analysed and the results are shown in table 1. Ages ranged from 0–18 years and 58% were male. The expected frequency of the codon 52 mutation (0.05) was observed in the total group. The frequencies of codon 54 (0.1) and codon 57 (0.05) mutations were lower than expected. However, when the frequencies were corrected for the ethnic composition of the sample (African/Caribbean 21%; Caucasian/Asian/Oriental 79%) the expected frequencies for codon 54 in the Eurasian group (0.12) and codon 57 in Afro-Caribbeans (0.22) were obtained.

One child was a codon 57 mutant homozygote, two were codon 54 mutant homozygotes whereas the Hardy Weinberg equation predicted 6 codon 54 homozygotes in this population. However, 16 were phenotypic homozygotes having combinations of mutant 52, 54 or 57 alleles, thus, a total of 19 children (3%) were considered homozygous for MBP mutations.

We first examined the association of mutant alleles with infection. Of 272 children without infection (controls), 64 carried mutant MBP alleles and 208 were wild type. In contrast, of 354 children with infections, 152 carried mutant MBP alleles and 202 were wild type (table 1). The increased frequency of mutant MBP alleles in infected children was highly significant (p<$10^{-6}$, odds ratio 2.4, 95% confidence limits 1.7 to 3.5). We next examined whether mutant MBP alleles increased susceptibility to infection both in heterozygotes and homozygotes (FIG. 1).

60 controls were heterozygous for mutant MBP alleles and 208 were wild type whereas 137 with infection were heterozygous for mutant MBP alleles and 202 were wild type (p=0.000004, odds ratio 2.4, 95% confidence limits 1.6 to 3.4). Although the number of homozygotes was inevitably much smaller a significant difference was still observed. Among controls, 4 were homozygous for mutant MBP alleles whereas in the infection group 15 were homozygous for mutant MBP alleles (p=0.02, odds ratio 3, 95% confidence limits 1.2 to 12.1). Homozygous children presented with strikingly severe infections including 6 with septicaemia, 2 with cellulitis and boils and 4 with severe tonsilitis and otitis media (see table 2).

We then examined whether the risk of infection conferred by mutant MBP alleles was related to the age of the children. The data is shown in table 2. This showed that mutant MBP alleles conferred significant susceptibility to infection in children aged less than 6 months (p=0.05, odds ratio 3, 95% confidence limits 1 to 9), in those aged 6–18 months (p=0.03, odds ratio 4, 95% confidence limits 1 to 17), and those aged more than 18 months (p=0.0001, odds ratio 2.4, 95% confidence limits 1.5 to 3.7).

The frequency of mutant MBP alleles in different infections varied widely. For example, only 13% of children with tuberculosis had mutant MBP alleles whereas 70% of children with streptococcal infections carried mutant MBP genes. Finally, an unexpected finding in the control group was that whereas 23% of the 270 controls carried mutant MBP alleles, 48% of the subgroup of 21 premature babies had MBP mutations and 2 were homozygotes (see table 2).

Discussion

Mannose binding protein is an important component of natural immunity which mediates opsonization following binding to mannose and N-acetylglucosamine residues on microbial cell walls. Mutations in the MBP gene impair opsonization and in small series have been associated with recurrent and severe infections in children and adults (Sumiya et al, (1991), supra; Summerfield et al, (1995), supra; Garred et al, (1995), supra).

However, both childhood infections and MBP mutations are common and up until now no link has been established between the presence of MBP mutations and susceptibility to childhood infection. The data presented herein establishes such a link and clearly indicates that testing to establish the presence (or absence) of MBP mutations will provide an indication of a child's susceptibility to infection, and indeed should provide an indication of susceptibility to recurrent infection.

Previous work in the area of MBP mutations has suggested that their presence leads to lowered levels of circulating MBP which in turn accounts for observed impaired opsonization. However, in the work described herein we relied on genotyping rather than measurements of serum MBP levels since such estimates appear to be unreliable predictors of MBP mutations (Lipscombe et al, (1992), supra; Lipscombe et al, (1995), supra; Madsen et al, (1994), supra; Madsen et al, (1995), supra). Although codon 54 and 57 mutations are associated with profoundly reduced levels of serum MBP some heterozygotes will have serum MBP levels within the normal range. Codon 52 mutations also lower serum MBP levels (Madsen et al, (1994), supra).

Overall, the data showed a striking association of infection with mutant MBP genotypes which was highly significant. Mutant MBP alleles were present in about twice as many children with infections as in control children. Furthermore, in contrast to a recent study of patients with suspected immunodeficiency (Madsen et al, (1995), supra) children who were heterozygous for mutant MBP alleles were also at a greatly increased risk of infection (p=0.000004) compared with controls. An increased frequency of infection in heterozygotes was still observed when codon 52 mutation data (p=0.02) and codon 54 data (p=0.005) were analysed separately.

The frequency of children homozygous for mutant MBP alleles in this group was 3%. Most of these children (16/19) were phenotypic homozygotes with combinations of mutant 52, 54 or 57 alleles. One was a codon 57 homozygote, which is the frequency predicted by the Hardy Weinberg equation, but only two were codon 54 homozygotes (0.003%) where the Hardy Weinberg equation predicted that there should be six. While the sample was not large enough to determine whether this difference was statistically significant the data is consistent with earlier reports (Lipscombe et al, (1992), supra; Madsen et al, (1994), supra) that Caucasoid populations are relatively depleted of codon 54 homozygotes. The reasons for this apparent depletion are obscure but could be due to recurrent miscarriage of affected fetuses (Kilpatrick et al, *Human Reproduction*, 10:2501–2505 (1995)) or to problems in neonatal life. In this context, it is interesting to note that whereas 23% of the non-infected control group carried mutant MBP alleles, 48% of the subgroup of 21 premature babies had MBP mutations and 2 were homozygotes (10%) of whom 1 died (see table 2). It can thus be seen that this apparent link also opens up the possibility of testing either a fetus or a new born baby to determine its MBP mutationm status as a guide to potential problems.

EXAMPLE 2

Methods

Consecutive patients with chronic HBV infections who had blood samples taken for clinical reasons were included in the study and in these patients surplus blood was used for the MBP assay. Patients with multiple viral infections were excluded as were two patients with agammaglobulinaemia. Nineteen Caucasian patients with acute or recovered infection (HBsAg and IgM anti HBc positive on presentation and clearing HBsAg within six months or anti HBc and anti HBs positive with normal transaminases), four of whom had a fulminant course and seventy patients with chronic hepatitis (HBsAg positive for greater than 6 months) were studied. Of those with chronic infection, forty-nine were male, the mean age was 39 years, and the majority of patients (49) had evidence of on-going viral replication (HBeAg positive). Seventeen were HBeAg negative with no detectable HBV DNA in serum. Two patients were infected with the HBe negative variant of HBV. The patients with chronic infection were a mixture of Caucasian, Asian and other groups (table 1). Control samples were obtained from 98 adult British Caucasian and 123 Chinese (Hong Kong) office workers.

Serological markers (HBsAg and HBeAg) were assayed using standard immunoassays (Abbott Diagnostics) as recommended by the manufacturer.

Genomic DNA was extracted from blood and exon 1 of the MBP gene amplified by PCR. The three mutations previously described were analysed by sequence specific oligonucleotide hybridisation (Wordsworth et al, *Immunogenetics*, 32:413–418 (1990)). The codon 52 mutation was confirmed by site-directed mutagenesis (SDM) PCR (Madsen et al, (1994), supra) and by direct DNA sequencing of the PCR products. All PCR assays were performed with appropriate positive and negative controls and samples were batched so that each experiment contained both infected and uninfected patient's samples. Serum MBP concentrations were measured using an ELISA assay (Lipscombe et al, *Eur. J. Hum. Genetics*, 4:13–19 (1996))

Results

The frequency of the codon 52 allele was 0.08 in the Caucasin patients with acute hepatitis B compared to 0.02 in the Caucasian controls. One patient with acute hepatitis B took approximately 6 months to clear the HBs antigen: this patient was homozygous for the codon 52 mutation.

In Caucasian but not Asian subjects, there was a highly significant association between the presence of the codon 52 mutation allele and chronic HBV infection (p=0.0004). The frequency of this allele in persistently HBV infected patients was 0.17 and 0.03 compared to frequencies of 0.02 and 0.01 respectively in the control Caucasian and Asian populations (table 2). There was no association of the codon 54 and 57 mutation alleles with acute or chronic HBV (table 2).

Three patients, one with acute and two with chronic infection, were genotypically homozygous for the codon 52 mutation and one patient with acute hepatitis was homozygous for the codon 54 mutation (table 1).

Serum samples from 25 of the Caucasian patients with chronic HBV were available to assay the concentration of MBP (table 3). Patients heterozygous for the variant MBP alleles (codon 52 and 54) had diminished serum concentrations consistent with genotypes.

TABLE 1

Observed genotypes in patients with acute or chronic hepatitis and HBsAg negative controls

| PATIENT GROUP | ETHNIC GROUP | TOTAL | WILD TYPE | CODON 52 HOMO ZYGOTE | CODON 52 HETERO ZYGOTE | CODON 54 HOMO ZYGOTE | CODON 54 HETERO ZYGOTE | CODON 57 HOMO ZYGOTE | CODON 57 HETERO ZYGOTE |
|---|---|---|---|---|---|---|---|---|---|
| CONTROL | CAUCASIAN | 98 | 61 | — | 4 | — | 33 | — | — |
|  | ASIAN | 117 | 88 | — | 2 | — | 27 | — | — |
| ACUTE HBV | CAUCASIAN | 19 | 13 | 1 | 1 | 1 | 2 | — | — |
| CHRONIC HBV | CAUCASIAN | 33 | 19 | 2 | 7 | — | 5 | — | — |
|  | ASIAN | 20 | 11 | — | 1 | — | 8 | — | — |
|  | OTHER | 17 | 2 | — | 1 | — | 3 | — | 4 |

TABLE 2

Allele frequencies in patients with acute or chronic hepatitis and HBsAg negative controls

| PATIENT GROUP | ETHNIC GROUP | n | WILD TYPE | CODON 52 | CODON 54 | CODON 57 |
|---|---|---|---|---|---|---|
| CONTROL | CAUCASIAN | 98 | 0.81 | 0.02 | 0.17 | — |
|  | ASIAN | 117 | 0.01 | 0.01 | 0.12 | — |
| ACUTE HBV | CAUCASIAN | 19 | 0.01 | 0.08 | 0.11 | — |
| CHRONIC HBV | CAUCASIAN | 33 | 0.76 | 0.17* | — | — |
|  | ASIAN | 20 | 0.77 | 0.03 | — | — |
|  | OTHER | 17 | 0.76 | 0.03 | 0.12 | — |

*$x^2$ test; P = 0.0004, compared to group

TABLE 3

Serum MBP levels in Caucasian patients with chronic HBV infection for whom serum samples were available

| GENOTYPE | n | MEDIAN (ng/ml) | INTERQUARTILE RANGE (ng/ml) | P VALUES* |
|---|---|---|---|---|
| WILD TYPE | 12 | 1030 | 775.5–1225.0 | |
| 52 HETEROZYGOTES | 9 | 670 | 270.0–1530.0 | 0.2555 |
| 54 HETEROZYGOTES | 4 | 140 | 40.0–337.5 | 0.0053 |

Discussion

28% of Caucasian patients with persistent HBV infection were homozygous or heterozygous for the codon 52 MBP allele, while only 11% of patients with acute infection and 4% of control subjects carried this allele. In contrast, only 5% of a group of Asian patients with chronic HBV were positive for the same allele, compared to 2% of Asian control subjects.

MBP facilitates the uptake of glycoproteins bearing terminal mannose residues by phagocytic cells bearing the collectin receptor. MBP binding to glycoproteins on yeast facilitates phagocytosis and the failure of serum from some patients to opsonise these particles is due to MBP deficiency. Such an opsonic effect has been described in patients with chronic HBV infection (Munoz, (1989), supra). How MBP influences the clearance of HBV is unknown. The middle envelope protein of HBV has an asparagine at position 4 that is glycosylated with an oligosaccharide which is, in part, mannose terminated (Gerlich, (1993), supra).

Therefore, it is possible that viral particles will be opsonised by normal serum MBP. The increased frequency of the codon 52 mutation in patients with chronic HBV infection is consistent with the possibility that the mutation impairs opsonisation and phagocytosis of HBV, as it does with yeast. However, the absence of an association between persistent HBV infection and the codon 54 and 57 mutant alleles, which result in markedly diminished serum concentrations of MBP, suggests that the reduction in the serum concentration of MBP in patients with the codon 52 mutant allele is insufficient to explain the disease association.

The codon 52 mutation (a cysteine for arginine substitution) differs from the other two mutations (which replace axial glycines with dicarboxylic acids) and presumably this mutation, which has a lesser effect on serum MBP concentrations but is associated with bacterial infections, prevents MBP from functioning as an opsonin. It is possible that the codon 52 variant MBP binds to HBV, fails to facilitate uptake by phagocytic cells but enhances uptake by hepatocytes thereby increasing the infective load in the liver. An alternative explanation for this association, is that the codon 52 mutation in the MBP gene is linked to mutations in another unidentified gene which is in linkage disequilibrium with the MBP locus and influences the host response to HBV.

In Caucasian patients with persistent HBV infection in whom the highest frequency of the codon 52 allele was seen, HBV infection is usually acquired in adult life due to sexual contact, or exposure to blood during IV drug use. In this group the infecting inoculum is small and in this situation defects in opsonic function may be critical in influencing outcome, the lower frequency of the 52 allele in Asian patients may relate to the fact that these people are usually infected at birth, the infecting inoculum may be larger, and in this situation all subjects become persistently infected as a result of the induction of T-cell tolerance by secreted HBe antigen which crosses the placenta. Against this backcloth genetic factors will be less important.

The presence of the codon 52 mutation is clearly linked to persistent HBV infection in Caucasian but not in Asian and African populations. The codon 52 allele in the African population is rare (Madsen et al, (1994), supra) possibly because of the survival disadvantage conferred by this allele in a region where HBV is endemic. Additional genetic factors, such as the presence of the MHC class II allele DRB1 1302, appear to influence whether infection is transient or persistent in Africans (Thursz et al, *New England journal of Medicine,* 332:1065–1069 (1995)). In the majority of Asians, infection is aquired at birth and virtually all these children become persistently infected because of exposure to HBe antigen at birth or before birth resulting in induction of T-cell tolerance. In Caucasian and African subjects infection is usually in adult life abd in childhood and between 5 and 20% respectively become persistently infected. It is in these groups that this study indicates that genetic factors influence outcome.

EXAMPLE 3

Materials and Methods

Whole blood samples were collected into potassium-EDTA and stored at −70° C. until DNA extraction. Exon 1 of the MBP gene was amplified by PCR to yield a product of 328 bp. The mutations were identified by sequence specific oligonucleotide hybridisation. Codon 52 mutations were confirmed by site directed mutagenesis PCR (Madsen et al, (1994), supra). Mutations were confirmed by DNA sequencing after asymmetric PCR to produce single stranded DNA using a complementary primer and Sequenase (Cambridge Bioscience).

Patients

Patients were reviewed following referral by their general practioner or hospital physician with a possible diagnosis of chronic fatigue syndrome. All patients underwent a detailed history, clinical examination, routine blood tests and urinalysis. Of fifty-five consecutive patients, a diagnosis of chronic fatigue syndrome was excluded in two because of concurrent depressive disease.

Blood samples were therefore obtained from the remaining fifty-three patients with a clinical diagnosis of chronic fatigue syndrome according to the latest international classification (Fukuda, et al, *Ann. Inter. Med.,* 121:953–959 (1994)). The revised case criteria for diagnosis of chronic fatigue syndrome are defined by:

(a) six months of persistent or relapsing fatigue where no other cause is apparent by careful history taking, examination, routine blood screening (full blood count, ESR, thyroid function tests, electrolytes, liver function tests, calcium, phosphorus, glucos and urinalysis); and (b) the concurrent occurrence of four or more of the main associated symptoms: (i) impaired short term memory or concentration; (ii) sore throat; (iii) tender cervical or axillary lymph nodes; (iv) myalgia or arthralgia; (v) "new" headaches; (vi) unrefreshing sleep; (vii) post-exertional malaise lasting for more than 24 hours. The diagnosis of chronic fatigue syndrome is excluded by: (i) active current medical conditions associated with fatigue; (ii) past medical conditions where there is clinical doubt about their resolution; (iii) current or past diagnosis of a major psychiatric disorder; (iv) significant history of alcohol or other substance abuse; (v) severe obesity (body mass index equal to or greater than 45 kg/m$^2$).

Results

Fifty-three caucasian CFS patients were genotyped. Nine (18%) had codon 52 mutation which was significantly greater than 4% codon 52 mutation in British blood donor controls (P=0.04, chi square).

Discussion

The findings indicate that chronic fatigue syndrome occurs in patients with a mutation in codon 52 of the MBP gene. It is possible that this genetic defect has predisposed these patients to recurrent and/or chronic viral infection. Chronic fatigue syndrome is characterised by six or more months of physical and mental fatigue with other symptoms including myalgia (Fukuda, et al, supra). Many patients describe an initial influenza or glandular fever-like illness as the possible trigger.

The subjective nature of the condition has limited research and there has been considerable debate about the nature of the syndrome (David, et al, *Br. Med. J.,* 296:696–698 (1988)). Many of the symptoms overlap with those of depressive disease or somatisation disorder and a high prevalence of pyschiatric disorder has been noted in this patient group.

Well documented outbreaks (Ramsay, A. M., O'Sullivan, E., *Lancet,* :761–764 (1956)) have given epidemiological support for a viral aetiology but even in this setting symptoms have been attributed to mass hysteria (McEvedy, C. P., Beard, A. W., *Br. Med. J.,* 1:7–11 (1970)).

Serological studies have often supported the concept of a viral aetiology. Several groups have suggested involvement of herpes infection—Epstein—Barr virus infection (Tobi, et al, supra) and, more recently, human herpes type 6. Other groups have reported data supporting the presence of an ongoing enteroviral infection with VP1 antigen in the serum of patients (Yousef, et al, *Lancet,* :146–150 (1988)).

Moreover, the use of PCR has supported the role of enteroviral infection by allowing the demonstration of viral nucleic acid in muscle biopsies (Archard, et al, *J. Roy. Soc. Med.,* 81:326–329 (1988)) and serum from patients with CFS (Clements, et al, *J. Med. Virol.,* :156–161 (1995)). Further support for the involvement of this group of viruses stems from the group of virus studies from the Glasgow group's demonstration of a possible novel enteroviral infection by serological assays in their patients (Galbraith, et al, *J. Gen. Virol.,* 76:1701–1707 (1995)).

Host factors have also been studied, but, until now, despite intensive immunological studies of lymphocyte subset and function, no consistent abnormalities have been demonstrated. Treatment with acyclovir (Straus, et al, *N. Eng. J. Med.,* 319:1692–8 (1988)) demonstrated no benefit and immunoglobulin infusions have given no consistent results (Peterson, et al, *Am. J. Med.,* 89:554–560 (1990); Lloyd, et al, *Am. J. Med.,* 89:561–568 (1990)). However, more recently, a pilot study with interferon has suggested that this may be of benefit for a subgroup of patients (Brook, et al, *J. Infect. Dis.,* 168:791–2 (1993)).

Mannose binding proteins are part of the non-specific immune response and are therefore part of the first host defences against pathogens. They are synthesised by hepatocytes and bind to carbohydrates on a variety of bacterial, fungal and viral pathogens. When binding occurs, complement is activated. Their action depends on their 3-D structure and it has recently been demonstrated that mutations in the gene, located on the tenth chromosome, can result in defective polymerisation. The high incidence of the codon 52 mutation in our patients suggests a causative link with chronic fatigue syndrome and supports the theory of an underlying host immunodeficiency predisposing to chronic infection, with a range of viruses being the cause of the syndrome. Such a hypothesis would explain the apparent involvement of a range of viruses.

What is claimed is:

1. A method of predicting whether Hepatitis-B virus (HBV) infection in an adult will lead to chronic persistent HBV infection which comprises a step of determining whether the adult carries a codon 52 mutation of the mannose binding protein (MBP) gene.

2. The method as claimed in claim 1 which is carried out on DNA derived from a biological sample obtained from the adult.

3. The method as claimed in claim 2 wherein the biological sample is blood.

4. The method as claimed in claim 1 wherein the exon 1 region of the MBP gene is subjected to amplification.

5. The method as claimed in claim 4 wherein the amplification step employs the following pair of primers:

5' primer: 5'GCACCCAGATTGTAGGACAGAG-3' (SEQ ID NO:1); and

3' primer: 5'CAGGCAGTTTCCTCTGGAAGG-3' (SEQ ID NO:2).

6. The method as claimed in claim 4 wherein the exon 1 region of the MBP gene is subjected to amplification by PCR.

7. The method as claimed in claim 1 wherein the genotype of the adult is determined.

8. The method as claimed in claim 7 wherein the genotype determination is carried out by means of sequence-specific oligonucleotide (SSO) dot-blot hybridization.

9. The method as claimed in claim 8 wherein the SSO dot-blot hybridization step employs one or more of the following primers:

5'-GATGGGCGTGATG-3' (SEQ ID NO:3); or

5'-GATGGGTGTGATG-3' (SEQ ID NO:4).

10. A kit for use in the method defined in claim 1, comprising a pair of primers for the PCR amplification of the exon 1 region of the MBP gene, the pair of primers being as follows:

5' primer: 5'-GCACCCAGATTGTAGGACAGAG-3' (SEQ ID NO:1); and

3' primer: 5'-CAGGCAGTTTCCTCTGGAAGG-3' (SEQ ID NO:2).

11. A kit as claimed in claim 10 which further comprises one or more reagents/materials for use in establishing the genotype of the MBP genotype of the adult.

12. A kit as claimed in claim 11 wherein the reagent for use in establishing MBP genotype comprises a primer selected from the following:

5'-GATGGGCGTGATG-3' (SEQ ID NO:3); or

5'-GATGGGTGTGATG-3' (SEQ ID NO:4).

13. A method of predicting the susceptibility of an adult to development of chronic Hepatitis-B virus (HBV) infection which comprises a step of determining whether the adult carries a codon 52 mutation of the mannose binding protein (MBP) gene.

14. A method as claimed in claim 13 which is carried out on DNA derived from a biological sample obtained from the adult.

15. The method as claimed in claim 14 wherein the biological sample is blood.

16. A method as claimed in claim 13 wherein the exon 1 region of the MBP gene is subjected to amplification.

17. The method as claimed in claim 16 wherein the amplification step employs the following pair of primers:

5' primer: 5'GCACCCAGATTGTAGGACAGAG-3' (SEQ ID NO:1); and

3' primer: 5'CAGGCAGTTTCCTCTGGAAGG-3' (SEQ ID NO:2).

18. A method as claimed in claim 16 wherein the exon 1 region of the MBP gene is subjected to amplification by PCR.

19. The method as claimed in claim 13 wherein the step of determining comprises determining the adult's genotype.

20. The method as claimed in claim 19 wherein the genotype determination is carried out by means of sequence-specific oligonucleotide (SSO) dot-blot hybridization.

21. The method as claimed in claim 20 wherein the SSO dot-blot hybridization step employs one or more of the following primers:

5'-GATGGGCGTGATG-3' (SEQ ID NO:3); or

5'-GATGGGTGTGATG-3' (SEQ ID NO:4).

22. A kit for use in the method defined in claim 13, comprising a pair of primers for the PCR application of the exon 1 region of the MBP gene, the pair of primers being as follows:

5' primer: 5'-GCACCCAGATTGTAGGACAGAG-3' (SEQ ID NO:1); and

3' primer: 5'-CAGGCAGTTTCCTCTGGAAGG-3' (SEQ ID NO:2).

23. The kit as claimed in claim 22 which further comprises one or more reagents/materials for use in establishing the genotype of the MBP genotype of the adult.

24. A kit as claimed in claim 23 wherein the reagent for use in establishing MBP genotype comprises a primer selected from the following:

5'-GATGGGCGTGATG-3' (SEQ ID NO:3);
5'-GATGGGTGTGATG-3' (SEQ ID NO:4).

* * * * *

SEQUENCE LISTING

<160> NUMBER OF SEQ ID NOS: 8

<210> SEQ ID NO 1
<211> LENGTH: 22
<212> TYPE: DNA
<213> ORGANISM: Artificial Sequence
<220> FEATURE:
<223> OTHER INFORMATION: Description of Artificial Sequence: unknown

<400> SEQUENCE: 1
gcacccagat tgtaggacag ag                                              22

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: unknown

<400> SEQUENCE: 2
caggcagttt cctctggaag g                                               21

<210> SEQ ID NO 3
<211> LENGTH: 13
<212> TYPE: DNA
<213> ORGANISM: Artificial Sequence
<220> FEATURE:
<223> OTHER INFORMATION: Description of Artificial Sequence: unknown

<400> SEQUENCE: 3
gatgggcgtg atg                                                        13

<210> SEQ ID NO 4
<211> LENGTH: 13
<212> TYPE: DNA
<213> ORGANISM: Artificial Sequence
<220> FEATURE:
<223> OTHER INFORMATION: Description of Artificial Sequence: unknown

<400> SEQUENCE: 4
gatgggtgtg atg                                                        13

<210> SEQ ID NO 5
<211> LENGTH: 13
<212> TYPE: DNA
<213> ORGANISM: Artificial Sequence
<220> FEATURE:
<223> OTHER INFORMATION: Description of Artificial Sequence: unknown

<400> SEQUENCE: 5
gtgatggcac caa                                                        13

<210> SEQ ID NO 6
<211> LENGTH: 13
<212> TYPE: DNA
<213> ORGANISM: Artificial Sequence
<220> FEATURE:
<223> OTHER INFORMATION: Description of Artificial Sequence: unknown

<400> SEQUENCE: 6
gtgatgacac caa                                                        13

<210> SEQ ID NO 7
<211> LENGTH: 15

-continued

```
<212> TYPE: DNA
<213> ORGANISM: Artificial Sequence
<220> FEATURE:
<223> OTHER INFORMATION: Description of Artificial  Sequence: unknown

<400> SEQUENCE: 7
accaagggag aaaag                                                    15

<210> SEQ ID NO 8
<211> LENGTH: 15
<212> TYPE: DNA
<213> ORGANISM: Artificial Sequence
<220> FEATURE:
<223> OTHER INFORMATION: Description of Artificial  Sequence: unknown

<400> SEQUENCE: 8
accaaggaag aaaag                                                    15
```